United States Patent [19]
Carter

[11] 4,267,034
[45] May 12, 1981

[54] SEPARATING OLEFINS FROM PARAFFINS WITH DIMETHYL SULFOXIDE EXTRACTANT

[75] Inventor: Cecil O. Carter, Bartlesville, Okla.

[73] Assignee: Phillips Petroleum Company, Bartlesville, Okla.

[21] Appl. No.: 94,252

[22] Filed: Nov. 14, 1979

[51] Int. Cl.³ .................... C07C 7/10; C10G 21/02
[52] U.S. Cl. ................................ 208/323; 208/324; 585/811; 585/835; 585/839
[58] Field of Search ............... 208/321, 322, 324; 585/856, 839, 811, 835

[56] References Cited

U.S. PATENT DOCUMENTS

| | | | |
|---|---|---|---|
| 2,365,898 | 12/1944 | Morris et al. | 585/856 |
| 2,936,283 | 5/1960 | Hutchings | 208/321 |
| 3,005,032 | 10/1961 | Makin | 585/856 |
| 3,050,573 | 8/1962 | Anderson et al. | 585/856 |
| 3,177,263 | 4/1965 | Francis | 208/321 |
| 3,526,587 | 9/1970 | O'Connor | 208/321 |
| 3,755,154 | 8/1973 | Akabayashi et al. | 208/323 |
| 3,810,951 | 5/1974 | Riordan | 585/839 |

FOREIGN PATENT DOCUMENTS 49-31866  8/1974  Japan.

OTHER PUBLICATIONS

"Hydrocarbon Processing", Nov. 1976, pp. 237 and 238.
"Hydrocarbon Processing", Aug. 1976, pp. 127 and 128.
"Chem. Eng.", Jan. 31, 1966, pp. 54 and 56.

*Primary Examiner*—Brian E. Hearn

[57] ABSTRACT

A method for separating olefins from paraffins in which a mixture of olefin and paraffin is contacted with a dimethyl sulfoxide (DMSO) extractant stream in the liquid phase thereby dissolving olefins in the DMSO and permitting separation of a paraffin stream. The DMSO containing dissolved olefin is then contacted with water and a phase separation is effected between olefin and a mixture of DMSO and water. At least a portion of the DMSO and water mixture can be fractionated to produce a dried DMSO product which can be recycled as a portion of the extractant into contact with the mixture of olefin and paraffin.

6 Claims, 1 Drawing Figure

SEPARATING OLEFINS FROM PARAFFINS WITH DIMETHYL SULFOXIDE EXTRACTANT

BACKGROUND OF THE INVENTION

This invention relates to an extraction process. In one of its aspects this invention relates to the use of dimethyl sulfoxide as an extractant. In another of its aspects, this invention relates to a process of phase separation for separating olefin and dimethyl sulfoxide (DMSO) in the presence of water. In still another aspect of the invention it relates to the fractionation of a mixture of DMSO and water to obtain a dried DMSO product.

Various processes are known which have as a product a stream containing a mixture of an olefin and the paraffin that corresponds in number of carbon atoms in the molecule to that olefin. Such mixtures are usually difficult to separate because boiling points of the components of the mixture are in a range that make distillation difficult, if not impossible. Such mixtures are, therefore, usually separated by an extraction process. Although the extraction processes permit the separation of the olefin and paraffin, the separation of the extractant from the component that it has dissolved from the original mixture to provide an economical process for recycling extractant through the separation system can require the expenditure of a great amount of energy. In the present invention a process is proposed that realizes considerable energy savings over conventional separation processes.

It is therefore an object of this invention to provide a method for separating olefins and paraffins that is energy efficient. It is another object of this invention to provide an integrated system for the extraction of olefins from a stream containing paraffins and olefins.

Other aspects, objects and the various advantages of this invention will become apparent upon studying this specificaton, the drawing, and the appended claims.

STATEMENT OF THE INVENTION

According to the invention, a method is provided for separating olefins from paraffins of corresponding carbon atom content. By this method a mixture of the olefin and paraffin is contacted in liquid phase with dimethyl sulfoxide (DMSO) as the extractant stream, contacting an amount of DMSO with the olefin/-paraffin mixture for a time sufficient to dissolve the olefin in the DMSO stream and therafter separating the paraffin from the DMSO which contains dissolved olefin.

The invention is further embodied in contacting with water the DMSO which contains dissolved olefin thereby effecting a phase separation of the contacting mixture into (1) olefin and (2) DMSO and water mixture so that the olefin is separated from the mixture of DMSO and water. At least a portion of this mixture can then be fractionated to produce a dried DMSO product. This dried product can then be recycled along with a portion of the mixture of DMSO and water to provide the extractant for contacting with the olefin and paraffin mixture for which a separation is sought.

This invention is particularly useful in the separation of olefins from close boiling paraffins having the same number of carbon atoms in the molecule in a range of about 5 to about 10 carbon atoms per molecule. In this manner olefins such as octene-1, octene-2, octene 3, hexene-1, hexene 2, hexene 3 and pentene-2 can be separated from the corresponding paraffin such as n-octane, n-hexane, and n-pentane.

The extraction step used in the present invention can comprise any suitable liquid-liquid extraction apparatus. Any convenient mode of contact such as batch or continuous can be used. Continuous countercurrent is presently preferred. The operating conditions can be any combination of conditions which effect the desired degree of absorption of olefins into the liquid DMSO phase. The ratio of DMSO to the olefin-containing feed will depend in part on the amount of olefin present and can be any convenient ratio in the range of 10:1 to 200:1 which is sufficient to effect the desired degree of separation. To conserve energy, the smallest effective ratio for a given feed stream should be used.

The water dilution and settling step can comprise any convenient mixing and settling apparatus, batch or continuous. Any suitable conditions of time, temperature, pressure, etc. which will provide the desired degree of separation of olefins from the dissolved liquid phase into the gaseous phase can be used. The amount of water added to the olefin-containing extractant stream will be sufficient substantially to reduce the solubility of the olefin in that stream. Generally, the water content of the DMSO will be increased to a level in the range of from about 5.5 weight percent to about 20 weight percent based on the DMSO. To conserve energy the smallest effective amount of water addition for a given feed stream should be used.

The DMSO drying step can comprise any conventional apparatus and procedure for separating water from DMSO. Fractional distillation is particularly convenient.

In the process, water in the amount of about 0.5 to about 5 percent can be tolerated in the DMSO extractant without deleteriously affecting the optimum extraction conditions. A portion of the wet DMSO recovered from the phase separation in which olefins are recovered can then be recycled to the extraction zone along with DMSO that has been dried by fractionation. Since all of the wet DMSO does not need to be dried, a significant saving of drying energy can be realized over similar known processes.

BRIEF DESCRIPTION OF THE DRAWING

The invention can best be understood in conjunction with the drawing which is a schematic representation of the process of this invention.

Referring now to the drawing, which will be discussed in conjunction with a calculated example of the separation of a mixture of about 50 weight percent octene and 50 weight percent n-octane, the mixture of $C_8$ olefin and paraffin is injected through line 1 into a countercurrent extractor vessel 2 into which dimethyl sulfoxide (DMSO) is injected in a countercurrent direction through line 21. The vessel is sized to allow intimate contact of the extractant with the mixture to be separated with the ratio of extractant to olefin mixture feed in the range of about 10:1 to about 200:1 by volume, as set out above. Contact is made at a temperature in the range of about 60° F. to about 120° F. and at a pressure that maintains the materials in the liquid phase, i.e., a range of about 15 to about 50 psia.

Figure 1:
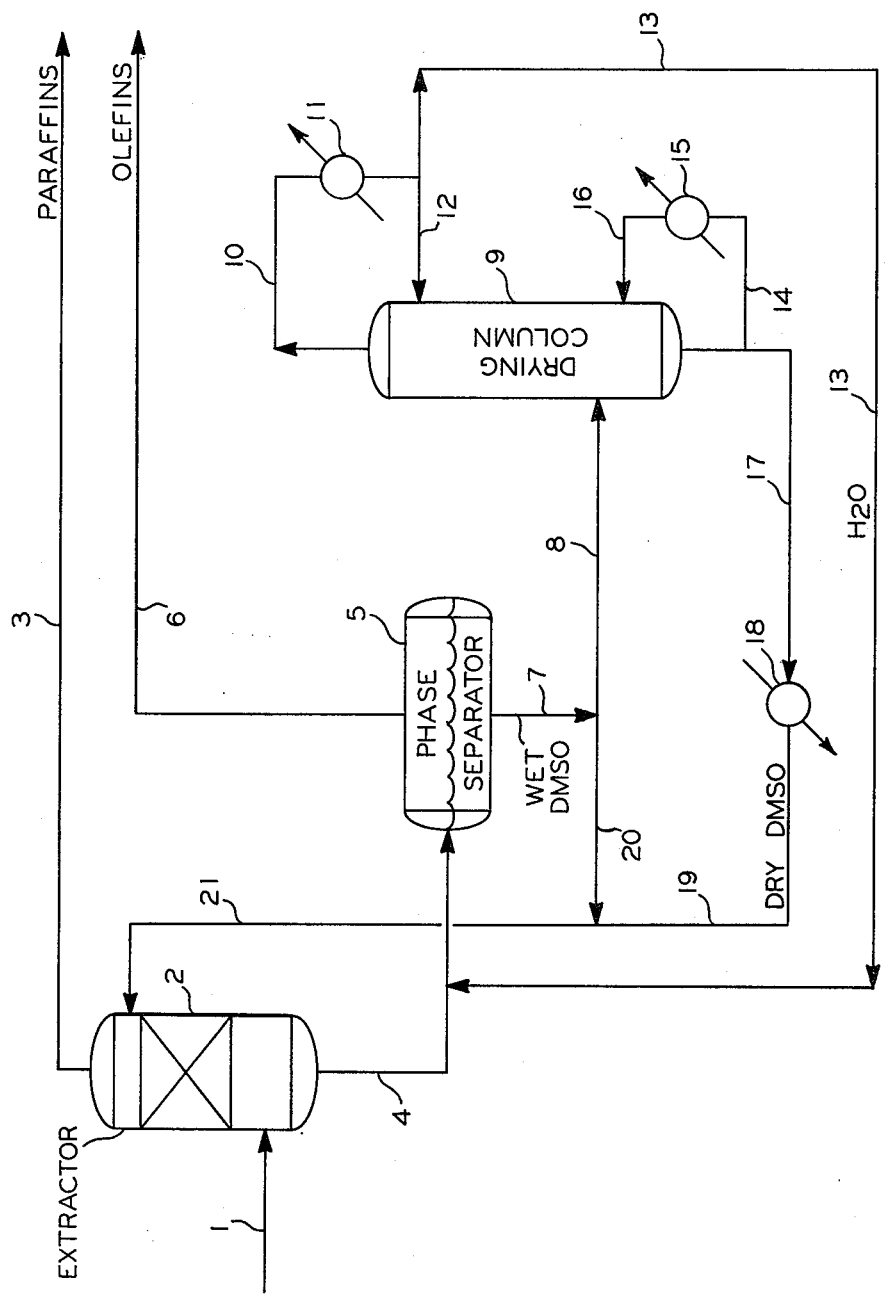

The raffinate stream, composed predominantly of paraffin, is removed by line 3. Typically, this stream will contain about 96 percent by weight paraffin with the remainder being minor amounts of olefin, water, and DMSO.

The extractant and contained extracted olefins are removed from the extraction zone 2 through line 4 and are mixed with water from line 13 in a ratio of about 12:1 to about 15:1 DMSO and olefin/water with this mixture then being transferred into phase separation zone 5.

The operating conditions of phase separation zone 5, temperature in the range of about 60° to about 120° F. and pressure in the range of about 15 to about 50 psia causes separation of olefin vapor from the mixture. The olefin is removed through line 6 with the stream typically containing about 98 percent olefin with the remainder being a minor amount of paraffin, water and DMSO. A wet DMSO stream containing minor amounts of olefin and paraffin is removed through line 7. The wet DMSO stream is split, with a portion being directed through line 8 into a fractionating column 9 from which water is removed overhead through line 10 through a condensor 11 with reflux returned to the fractionator through line 12 and water recycled through line 13 to be mixed with the extractant stream in line 4. Kettle liquid is passed through line 14 through reboiler 15 which supplies the heat for the fractionation operation and back through line 16 into the base of the fractionator 9. A dry DMSO stream is removed through line 17 through cooler 18 and line 19 to be mixed with a sufficient amount of wet DMSO from line 20 which has been removed through line 7 from the phase separator 5 so that DMSO containing an amount of water in the range of about 0.5 to about 5 percent by weight of total mixture is returned an extracted through line 21 into the extracting zone 2. Typical analyses for various streams in this process are:

| 1. | Feed, | 100 lb/hr |
| | Composition: | octene, 25 wt. % |
| | | n-octane, 75 wt. % |
| 3. | Overhead Product, | 77.7 lb/hr |
| | Composition: | octene, 4.12 wt. % |
| | | n-octane, 95.88 wt. % |
| 4. | Bottom Product, | olefins, 22.2 lb/hr |
| | Composition: | octene, 98.0 wt. % |
| | | n-octane, 2.0 wt. % |
| | | DMSO 10,889 lb/hr |
| | | water 115 lb/hr |
| 6. | Olefins, | 22.2 lb/hr |
| | Composition: | octene, 98.0 wt. % |
| | | n-octane, 2.0 wt. % |
| 7. | Wet DMSO, | DMSO, 10,890 lb/hr |
| | | water, 899.5 lb/hr |
| 13. | Water Recycle, | 784 lb/hr |
| 17. | Dry DMSO Recycle, | 9563 lb/hr |
| 21. | Total Extractant Recycle, | 11,005 lb/hr |
| | Composition: | DMSO, 99.0 wt. % |
| | | water, 1.0 wt. % |

I claim:

1. A method for separating olefins from paraffins of corresponding carbon atom content said method comprising:
   (a) contacting in liquid phase a mixture of said olefin and paraffin with a dimethyl sulfoxide extractant stream in an amount and for a time sufficient to dissolve olefins in the DMSO stream;
   (b) separating the paraffin from the DMSO which contains dissolved olefin;
   (c) contacting with water the DMSO which contains dissolved olefin, thereby causing a phase separation of the contacted mixture into
      (1) DMSO and water mixture and
      (2) olefin; and
   (d) separating said olefin from the DMSO and water mixture.

2. A method of claim 1 further comprising:
   (e) fractionating at least a portion of the DMSO and water mixture thereby producing
      (1) a water product and
      (2) a dried DMSO product.

3. A method of claim 2 further comprising:
   (f) cycling DMSO product to contact with a mixture of said olefin and said paraffin.

4. A method for separating olefins from paraffins of corresponding carbon content said method comprising:
   (a) contacting in liquid phase a mixture of said olefin and paraffin with a DMSO extractant stream in an amount and for a time sufficient to dissolve olefins in the DMSO stream;
   (b) separating the paraffin from the DMSO containing dissolved olefin;
   (c) contacting with water the DMSO containing dissolved olefin thereby causing a phase separation of the contacting mixture into
      (1) DMSO and water mixture, and
      (2) olefin;
   (d) separating said olefin from the DMSO and water mixture;
   (e) fractionating at least a portion of the DMSO and water mixture thereby producing a water product and a dry DMSO product; and
   (f) recycling the DMSO product to contact with a mixture of said olefin and said paraffin.

5. A method of claim 3 or 4 wherein both DMSO which contains water obtained from step (c) and DMSO from which water has been separated from step (f) are cycled to the extraction step.

6. A method of claim 5 wherein the total DMSO extractant stream comprises from about 0.5 percent to about 5 percent water.

* * * * *